(12) United States Patent
Nakamura et al.

(10) Patent No.: US 10,385,001 B2
(45) Date of Patent: Aug. 20, 2019

(54) METHOD OF PRODUCING TEREPHTHALIC ACID

(71) Applicant: Mitsubishi Gas Chemical Company, Inc., Chiyoda-ku (JP)

(72) Inventors: Goh Nakamura, Kurashiki (JP); Hideaki Fujita, Kurashiki (JP); Kotaro Murakami, Kurashiki (JP); Ryusuke Shigematsu, Chiyoda-ku (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 0 days.

(21) Appl. No.: 16/088,226

(22) PCT Filed: Mar. 7, 2017

(86) PCT No.: PCT/JP2017/008964
§ 371 (c)(1),
(2) Date: Sep. 25, 2018

(87) PCT Pub. No.: WO2017/169564
PCT Pub. Date: Oct. 5, 2017

(65) Prior Publication Data
US 2019/0169109 A1 Jun. 6, 2019

(30) Foreign Application Priority Data

Mar. 31, 2016 (JP) .................. 2016-071319

(51) Int. Cl.
*C07C 51/47* (2006.01)
*C07C 63/26* (2006.01)

(52) U.S. Cl.
CPC .............. *C07C 51/47* (2013.01); *C07C 63/26* (2013.01); *C07B 2200/13* (2013.01)

(58) Field of Classification Search
CPC ...... C07C 51/47; C07C 63/26; C07B 2200/13
See application file for complete search history.

(56) References Cited

U.S. PATENT DOCUMENTS 5,777,161 A 7/1998 Inary

FOREIGN PATENT DOCUMENTS

| JP | 55-87744 A | 7/1980 |
| JP | 57-53431 A | 3/1982 |
| JP | 7-149690 A | 6/1995 |
| JP | 10-45667 A | 2/1998 |
| JP | 2008-239608 A | 10/2008 |

OTHER PUBLICATIONS

International Search Report dated Apr. 25, 2017 in PCT/JP2017/008964 filed Mar. 7, 2017.

*Primary Examiner* — Jafar F Parsa
(74) *Attorney, Agent, or Firm* — Oblon, McClelland, Maier & Neustadt, L.L.P.

(57) ABSTRACT

A method of terephthalic acid production in which slurry of crude terephthalic acid obtained through liquid-phase oxidation of a p-phenylene compound or a terephthalic acid slurry resulting from catalytic hydrogenation of the crude terephthalic acid is introduced into an upper part of a dispersion medium replacement tower while a second dispersion medium for replacement is introduced from a lower part of the dispersion medium replacement tower to perform dispersion medium replacement. The method is capable of enabling the dispersion medium replacement tower to continue stable operation while maintaining an extremely high efficiency of dispersion medium replacement.

7 Claims, 1 Drawing Sheet

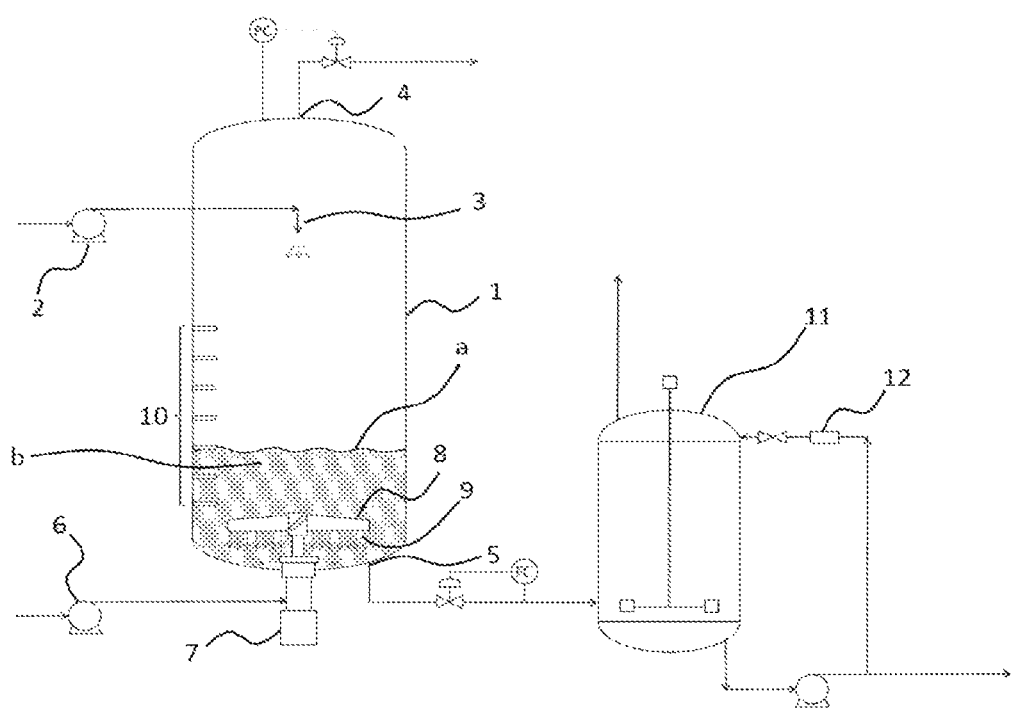

METHOD OF PRODUCING TEREPHTHALIC ACID

TECHNICAL FIELD

The present invention relates to methods of producing terephthalic acid. More particularly, the present invention relates to a method of producing high-purity terephthalic acid by replacing a dispersion medium of starting slurry. The present invention also relates to a method of producing terephthalic acid from starting slurry which is either crude terephthalic acid slurry obtained through a liquid-phase oxidation reaction and containing crystalline terephthalic acid particles, water, and a large amount of impurities or slurry obtained through catalytic hydrogenation or recrystallization of crude terephthalic acid, the method employing a dispersion medium replacement process capable of efficient replacement of the dispersion medium of such starting slurry with a second dispersion medium.

BACKGROUND ART

Terephthalic acid is produced by a liquid-phase oxidation reaction of p-phenylene compounds such as p-alkylbenzenes typified by p-xylene. The production of terephthalic acid generally uses acetic acid as a solvent and a catalyst such as cobalt and manganese, optionally with an added promoter such as bromine compounds or acetaldehyde. Since acetic acid is used as the solvent as mentioned above, the crude terephthalic acid slurry obtained through the liquid-phase oxidation reaction contains a large amount of impurities such as 4-carboxybenzaldehyde (4CBA), para-toluic acid (p-TOL), benzoic acid, and various other coloring impurities. Therefore, the crude terephthalic acid obtained by being separated from the slurry also contains these impurities, and a highly sophisticated purification technique is needed to obtain high-purity terephthalic acid.

Various methods for purifying crude terephthalic acid are known, such as a method in which terephthalic acid is dissolved in acetic acid, water, or mixed solvents thereof at high temperature and high pressure and the solution is then subjected to catalytic hydrogenation, decarbonylation, oxidation, or recrystallization and a method in which slurry having terephthalic acid crystals partially dissolved therein is subjected to high-temperature immersion. Both the production of crude terephthalic acid by a liquid-phase oxidation reaction and the purification of the crude terephthalic acid require a final procedure for separation of the terephthalic acid crystals from the dispersion medium.

Oxidation intermediates such as 4CBA, p-TOL, and benzoic acid or coloring substances which are present as impurities in the oxidation-derived slurry or the slurry resulting from purification of crude terephthalic acid are dissolved in the dispersion medium of the slurry at high temperature. Thus, when the slurry is cooled to around 100° C. to give slurry containing terephthalic acid crystals, these impurities are incorporated in the terephthalic acid crystals, with the result that it is difficult to obtain high-purity terephthalic acid.

Therefore, in order to separate terephthalic acid as pure as possible from the dispersion medium of the crude terephthalic acid slurry resulting from the oxidation reaction or the slurry resulting from the purification of crude terephthalic acid, the separation should be conducted under high-temperature, pressurized conditions. The method that is most commonly used to separate a dispersion medium from slurry containing crystals is centrifugation. The centrifugation is widely used also for slurries resulting from oxidation reaction and for slurries resulting from purification. The centrifugation is a method in which the slurry is introduced into a basket rotating at a high speed so as to cause the dispersion medium to overflow from the top of the basket while directing the crystals to the bottom of the basket. However, continuous operation at high temperature and high pressure is known to pose some difficulties arising from the structural and functional limitations of the centrifuge.

First, the crystals are difficult to rinse during the centrifugation or after the separation, and thus the amount of the dispersion medium adhered to the crystals tends to increase. A common method employed to solve this problem is to form a cake of the centrifugally separated terephthalic acid crystals into slurry with a fresh, hot solvent. This method, however, has the disadvantage of requiring several repetitions of the separation procedure. Furthermore, owing to the high-speed rotation at high temperature and high pressure, the maintenance of the centrifuge is so cumbersome and difficult that the cost of maintenance increases. The centrifugation cannot therefore be considered sophisticated as a technique for use in this field.

As a separation technique alternative to the centrifugation, a dispersion medium replacement apparatus making use of gravitational sedimentation of terephthalic acid crystals has been proposed. For example, Patent Literature 1 and Patent Literature 2 propose such apparatuses. According to Patent Literature 1, a lateral shelves with a plurality of holes are provided inside the dispersion medium replacement apparatus. It is stated that without such a structure, the efficiency of the replacement would be unsatisfactory due to channeling or back mixing of the fluid in the apparatus. In Patent Literature 2, a shelf plate forming a slope is provided to improve the replacement performance. However, when slurry is treated, in particular when slurry is subjected to dispersion medium replacement making use of gravitational sedimentation, the provision of such a shelf plate entails significant difficulty. Specifically, the slurry is sedimented on the shelves and clogs the holes, which requires a tremendous effort to stabilize the operation. These techniques can therefore never be considered sophisticated.

Dispersion medium replacement apparatuses requiring no shelf plates have also been proposed (Patent Literatures 3 and 4, for example). Such a dispersion medium replacement apparatus requiring no shelf plates has the following four inlets/outlets: (1) a supply port through which starting slurry consisting of a first dispersion medium and terephthalic acid crystals is supplied to an upper compartment of the apparatus; (2) a supply port through which a second dispersion medium is introduced into a lower compartment of the apparatus; (3) an outlet port through which mainly replaced slurry consisting of terephthalic acid crystals and the second dispersion medium is discharged from the lower compartment of the apparatus; and (4) an outlet port through which mainly the first dispersion medium is discharged from the upper compartment of the apparatus. The flow rates through these ports can be freely changed, except for the supply flow rate through the port (1). This provides flexibility of operation; however, control of the flow rates is considerably complicated since changing the flow rates influences the performance properties such as the efficiency of dispersion medium replacement. Thus, for example, Patent Literature 3 discloses that the dispersion medium replacement apparatus can easily be allowed to continue stable operation at a high replacement efficiency by adjusting the temperature distribution inside the dispersion medium replacement apparatus so as to render its upper part hotter and create a zone showing a sharp change in temperature and by controlling the amount of the second dispersion medium to be introduced and/or the amount of the replaced slurry to be discharged so as to keep this temperature zone at a desired position.

Patent Literature 4 mentioned above discloses that the change rate of terephthalic acid content per unit thickness (mass %/m) in a boundary region needs to be controlled to be 15 or more but 500 or less in order to significantly improve the replacement efficiency. However, when the amount of the second dispersion medium to be introduced and/or the amount of the replaced slurry to be discharged is controlled on the basis of the change rate of terephthalic acid content, it is necessary to know the terephthalic acid content in the dispersion medium replacement apparatus.

The terephthalic acid slurry supplied to the dispersion medium replacement tower is in the form of an aqueous slurry at around 140 to 190° C., while water at around 100° C. is supplied as the second dispersion medium from the bottom of the tower. Thus, the interior of the dispersion medium replacement apparatus is pressurized, and the density of terephthalic acid is difficult to measure through sampling depending on the height of the boundary region. Patent Literature 3 also discloses a method of detecting the terephthalic acid content in slurry with the aid of an on-line densitometer disposed in the pipe of the above outlet port (3) through which mainly the replaced slurry consisting of terephthalic acid crystals and the second dispersion medium is discharged or in the pipe designed to circulate the slurry into the dispersion medium replacement tower.

CITATION LIST

Patent Literature

Patent Literature 1: Japanese Unexamined Patent Application Publication No. 57-053431
Patent Literature 2: Japanese Unexamined Patent Application Publication No. 55-087744
Patent Literature 3: Japanese Unexamined Patent Application Publication No. 10-045667
Patent Literature 4: Japanese Unexamined Patent Application Publication No. 2008-239608

SUMMARY OF INVENTION

Technical Problem

In order for the dispersion medium replacement tower to stably maintain a high efficiency of dispersion medium, the position of the interfacial region (the zone showing a sharp change in temperature) of the upper portion of the slurry layer in the lower compartment of the replacement tower should be stabilized and, in addition, the terephthalic acid content of the slurry layer in the lower compartment of the replacement tower should be kept within a certain range. Controlling these factors within certain ranges necessitates detecting the terephthalic acid content in slurry in the lower compartment of the replacement tower. With the method described in Patent Literature 3 which detects the terephthalic acid content in slurry with the aid of an on-line densitometer disposed in the pipe of the outlet port through which the replaced slurry consisting of terephthalic acid crystals and the second dispersion medium is discharged or in the pipe designed to circulate the slurry into the dispersion medium replacement tower, the value measured by the densitometer significantly varies due to uneven slurry concentration in the lower compartment of the replacement tower, besides which crystals of terephthalic acid are sedimented on the densitometer during long-term operation and cause measurement error trouble. This method is therefore disadvantageous in that stable operation of the dispersion medium replacement tower is difficult.

An object of the present invention is to provide a method of terephthalic acid production in which slurry of crude terephthalic acid obtained through liquid-phase oxidation of a p-phenylene compound or a terephthalic acid slurry resulting from catalytic hydrogenation of the crude terephthalic acid is introduced into an upper part of a dispersion medium replacement tower while a second dispersion medium for replacement is introduced from a lower part of the dispersion medium replacement tower to perform dispersion medium replacement, the method capable of enabling the dispersion medium replacement tower to continue stable operation while maintaining an extremely high efficiency of dispersion medium replacement.

Solution to Problem

As a result of intensive investigations, the present inventors have found that an extremely high replacement efficiency can be stably obtained by providing a crystallization chamber at a stage subsequent to a dispersion medium replacement apparatus and maintaining the slurry amount in the crystallization chamber within a certain range while measuring the terephthalic acid content with a slurry densitometer provided in the crystallization chamber and keeping constant the slurry concentration in the crystallization chamber.

That is, the present invention is as follows.

[1]

A method of producing terephthalic acid, comprising steps of:

introducing starting terephthalic acid slurry into an upper part of a dispersion medium replacement tower, the starting terephthalic acid slurry containing a dispersion medium and crude terephthalic acid obtained through liquid-phase oxidation of a p-phenylene compound;

bringing the starting terephthalic acid slurry into contact with an upward flow of a second dispersion medium introduced from a lower part of the dispersion medium replacement tower to form, in a lower compartment of the dispersion medium replacement tower, a layer of slurry of a purified terephthalic acid crystal dispersed in the second dispersion medium;

discharging the slurry of the purified terephthalic acid crystal from the lower compartment of the dispersion medium replacement tower and delivering the slurry to a crystallization chamber provided with a unit for measuring slurry concentration; and delivering the slurry in the crystallization chamber to a solid-liquid separation unit to separate a terephthalic acid crystal, wherein the following conditions (1) to (3) are maintained by regulating a flow rate of the second dispersion medium supplied to the lower compartment of the dispersion medium replacement tower, a flow rate of the slurry of the purified terephthalic acid crystal which is discharged from the lower compartment of the dispersion medium replacement tower, and a flow rate of the slurry delivered from the crystallization chamber to the solid-liquid separation unit:

(1) volume $V_1$ of the slurry in the crystallization chamber is in a range of 0.050 to 0.80 times with respect to volume $V_0$ of the whole terephthalic acid slurry in the dispersion medium replacement tower;

(2) a position of an interfacial region between the layer of the slurry of terephthalic acid crystal which is formed in the lower compartment of the dispersion medium replacement tower and a dilute terephthalic acid slurry in a middle part of the dispersion medium replacement tower is in a variation range of ±800 mm from a control target level; and (3) the slurry concentration in the crystallization chamber is in a range of 25 to 40 mass %.

[2]

The method of producing terephthalic acid according to [1], wherein a stirrer is disposed in the lower compartment of the dispersion medium replacement tower, and the position of the interfacial region between the layer of the slurry of terephthalic acid crystal which is formed in the lower compartment of the dispersion medium replacement tower and the dilute terephthalic acid slurry in the middle part of the dispersion medium replacement tower is above an upper end of the stirrer in a range of 0.3 to 1.5 times with respect to an inner diameter of the replacement tower.

[3]

The method of producing terephthalic acid according to [1] or [2], wherein the slurry concentration in the crystallization chamber is kept in the range of 25 to 40 mass % by:

increasing a slurry flow rate of the slurry of the purified terephthalic acid crystal to be discharged from the lower compartment of the dispersion medium replacement tower upon increase in the concentration of the slurry in the crystallization chamber; and decreasing the slurry flow rate upon decrease in the slurry density.

[4]

The method of producing terephthalic acid according to any of [1] to [3], wherein the position of the interfacial region between the layer of the slurry of terephthalic acid crystal which is formed in the lower compartment of the dispersion medium replacement tower and the dilute terephthalic acid slurry in the middle part of the dispersion medium replacement tower is kept in the variation range of ±800 mm from the control target level by:

decreasing the flow rate of the second dispersion medium supplied to the lower compartment of the dispersion medium replacement tower upon elevation of the position of the interfacial region; and increasing the flow rate upon lowering of the position of the interfacial region.

[5]

The method of producing terephthalic acid according to any of [1] to [4], wherein the unit for measuring the slurry concentration in the crystallization chamber is a densitometer, and the densitometer is disposed in a pipe provided to discharge the slurry of the purified terephthalic acid crystal from the crystallization chamber and designed to circulate a part of the slurry into the crystallization chamber.

[6]

The method of producing terephthalic acid according to any of [1] to [5], wherein a plurality of thermometers are arranged in a vertical direction inside the dispersion medium replacement tower, and the position of the interfacial region between the layer of the slurry of terephthalic acid crystal which is formed in the lower compartment of the dispersion medium replacement tower and the dilute terephthalic acid slurry in the middle part of the dispersion medium replacement tower is detected by measuring a temperature change in the vertical direction inside the dispersion medium replacement tower.

[7]

The method of producing terephthalic acid according to any of [1] to [6], wherein the starting terephthalic acid slurry is slurry obtained by: forming crude terephthalic acid slurry through liquid-phase oxidation of a p-phenylene compound followed by depressurization and heating to high temperature; separating a reaction dispersion medium from the crude terephthalic acid slurry to obtain a crude terephthalic acid crystal; dissolving the crude terephthalic acid crystal in water at high temperature and high pressure; subjecting the resulting solution to catalytic hydrogenation; and subjecting the resulting reaction fluid to gradual depressurization and cooling using a multi-stage crystallization chamber to crystallize terephthalic acid.

Advantageous Effects of Invention

The present invention makes it possible, in a terephthalic acid production process using a dispersion medium replacement tower, to stabilize the position of an interfacial region of an upper portion of a slurry layer in a lower compartment of the dispersion medium replacement tower and to control the terephthalic acid content of the slurry layer in the lower compartment of the replacement tower within a certain range. This enables the dispersion medium replacement tower to operate at a high dispersion medium replacement efficiency over a long period of time.

BRIEF DESCRIPTION OF DRAWING

FIG. 1 illustrates a dispersion medium replacement apparatus used in examples.

DESCRIPTION OF EMBODIMENT

Hereinafter, an embodiment of the present invention (this embodiment will be simply referred to as "present embodiment" hereinafter) will be described in detail. The present embodiment described below is an example illustrative of the present invention and is not intended to limit the present invention to the contents of the following description. The present invention can be carried out with appropriate modifications falling within the gist of the invention.

A method of producing terephthalic acid according to the present embodiment comprises steps of:

introducing starting terephthalic acid slurry into an upper part of a dispersion medium replacement tower, the starting terephthalic acid slurry containing a dispersion medium and crude terephthalic acid obtained through liquid-phase oxidation of a p-phenylene compound;

bringing the starting terephthalic acid slurry into contact with an upward flow of a second dispersion medium introduced from a lower part of the dispersion medium replacement tower to form, in a lower compartment of the dispersion medium replacement tower, a layer of slurry of the purified terephthalic acid crystal dispersed in the second dispersion medium (this step may hereinafter be referred to as "dispersion medium replacement step");

discharging the slurry of the purified terephthalic acid crystal from the lower compartment of the dispersion medium replacement tower and delivering the slurry to a crystallization chamber provided with a unit for measuring slurry concentration; and delivering the slurry in the crystallization chamber to a solid-liquid separation unit to separate a terephthalic acid crystal.

Additionally, in the method of producing terephthalic acid according to the present embodiment, following conditions (1) to (3) are maintained by regulating a flow rate of the second dispersion medium supplied to the lower compartment of the dispersion medium replacement tower, a flow rate of the slurry of the purified terephthalic acid crystal which is discharged from the lower compartment of the dispersion medium replacement tower, and a flow rate of the slurry delivered from the crystallization chamber to the solid-liquid separation unit:

(1) volume $V_1$ of the slurry in the crystallization chamber is in a range of 0.050 to 0.80 times with respect to volume $V_0$ of the whole terephthalic acid slurry in the dispersion medium replacement tower;

(2) a position of an interfacial region between the layer of the slurry of terephthalic acid crystal which is formed in the lower compartment of the dispersion medium replacement tower and a dilute terephthalic acid slurry in a middle part of the dispersion medium replacement tower is in a variation range of ±800 mm from a control target level; and (3) the slurry concentration in the crystallization chamber is in a range of 25 to 40 mass %.

The crude terephthalic acid in the present embodiment is obtained through liquid-phase oxidation of a p-phenylene compound. The p-phenylene compound used has, at para positions, carboxyl groups and/or oxidizable substituents from which carboxyl groups can be produced through liquid-phase air oxidation. Examples of the oxidizable substituents include methyl, ethyl, propyl, isopropyl, aldehyde, and acetyl groups. The oxidizable substituents may be the same or different from each other.

The oxidant used for oxidation in a liquid phase is, for example, oxygen or air and is not limited to either of them. When the oxidation is carried out in acetic acid solution in the presence of a cobalt catalyst and a manganese catalyst and a bromine compound serving as a co-catalyst, it is sufficient to use air as the oxidant. When the oxidation is carried out in acetic acid solution in the presence of a cobalt catalyst, the oxidant is preferably oxygen.

When the catalyst used is a cobalt catalyst and a manganese catalyst, it is preferable to further use a bromine compound. Bromine compounds are generally considered to act as co-catalysts, and hydrogen bromide or sodium bromide is preferred. When a cobalt catalyst is used, it is preferable to further use acetaldehyde, methyl ethyl ketone, or the like as a promoter.

The oxidation reaction is carried out at high temperature and high pressure to promote the reaction. Typically, the reaction temperature is preferably 150 to 240° C., and the pressure is preferably 1 to 3 MPa.

Crude terephthalic acid obtained by liquid-phase oxidation in acetic acid solution generally contains many impurities such as 4-carboxybenzaldehyde (4CBA), and the OD 340, which is a measure of whiteness, of the crude terephthalic acid is not sufficient for it to be used by itself as a polymer material for molding. Thus, a post-treatment step such as impurity removal is required. The upper limits of the content of 4CBA and the content of other impurities in the crude terephthalic acid subjected to the post-treatment step are not particularly defined. The upper limit of the OD 340 in the post-treatment step is not particularly defined either.

The loss of acetic acid by burning due to oxidation reaction can be reduced by employing oxidation reaction conditions under which the 4CBA content will be somewhat high. Thus, considering the steps as a whole, it is advantageous to set conditions under which the 4CBA content in the crude terephthalic acid obtained by the liquid-phase oxidation step will be 500 ppm or more.

The crude terephthalic acid produced by oxidation reaction partially crystalizes and is present in the form of slurry in the reactor. This slurry is then subjected to a crystallization step in which the temperature and pressure are decreased gradually. After that, terephthalic acid crystals are separated from the acetic acid solvent by a solid-liquid separator. In the method of producing terephthalic acid according to the present embodiment, a dispersion medium replacement tower described later is provided for the crystallization step subsequent to the oxidation reaction so as to replace the dispersion medium (first dispersion medium) of the terephthalic acid slurry with another dispersion medium (second dispersion medium), and such a crystallization step is followed by solid-liquid separation. The second dispersion medium for replacing the dispersion medium of the terephthalic acid slurry resulting from oxidation reaction is preferably aqueous acetic acid or water.

The crude terephthalic acid obtained by oxidation reaction is then transferred to a catalytic hydrogenation step. Solution of the crude terephthalic acid is subjected to this catalytic hydrogenation, which is thus carried out at high temperature and high pressure to maintain the solution state. Water is commonly used as the solvent, and the catalytic hydrogenation temperature is 200° C. or higher and preferably in the range of 240 to 300° C. The concentration of the crude terephthalic acid is preferably in the range of 10 to 40 mass %. The pressure is preferably in the range of 30 to 80 atm in order to maintain the liquid phase and ensure a hydrogen partial pressure appropriate for the catalytic hydrogenation reaction.

A group VIII noble metal is suitably used as the catalyst for the catalytic hydrogenation reaction. Preferred as the group VIII noble metal are palladium, platinum, ruthenium, and rhodium, and more preferred are palladium and platinum. The group VIII noble metal used does not need to consist of one group VIII noble metal alone. Two or more group VIII noble metals may be used in combination if necessary.

The catalyst is generally preferably used in the form of being supported on a support, although the form of this catalyst is not necessarily limited to the form of being supported on a support. A porous body is typically used as the support. As to the material of the support, carbon-based materials are preferred, activated carbon is more preferred, and coconut shell charcoal is even more preferred. The range of the amount of the catalyst supported on the support is not particularly limited, since a small amount of the catalyst can be effective. In order to keep the activity over a long period of time, the amount of the catalyst supported on the support is preferably 0.1 to 0.5 mass %.

The molar amount of hydrogen for the catalytic hydrogenation is at least 2 times with respect to the molar amount of 4CBA. The time of catalytic hydrogenation only needs to be sufficient to substantially complete hydrogenation, and is typically in the range of 1 to 60 minutes, preferably 2 to 20 minutes. The catalytic hydrogenation is typically performed in a continuous scheme.

The crude terephthalic acid solution resulting from catalytic hydrogenation is filtered through a filter made of sintered titanium, another sintered metal, or carbon particles in order to prevent the contamination of fine powders produced from abrasion of the catalyst support used such as activated carbon. After that, the solution is introduced into a crystallizer consisting of two to six stages connected in series or into a batch crystallizer. The pressure is gradually decreased to cause water evaporation and thereby decrease the temperature to between 120 and 200° C., which results in formation of terephthalic acid crystal and hence slurry.

The starting terephthalic acid slurry in the present embodiment is preferably slurry obtained by: forming crude terephthalic acid slurry through liquid-phase oxidation of a p-phenylene compound followed by depressurization and heating to high temperature; separating a reaction dispersion medium from the crude terephthalic acid slurry to obtain a crude terephthalic acid crystal; dissolving the crude terephthalic acid crystal in water at high temperature and high pressure; subjecting the resulting solution to catalytic hydrogenation; and subjecting the resulting reaction fluid to gradual depressurization and cooling using a multi-stage crystallization chamber to crystallize terephthalic acid.

In the method of producing terephthalic acid according to the present embodiment, terephthalic acid crystal slurry containing a terephthalic acid crystal and a dispersion medium, which has been obtained from a middle-stage crystallizer in the multi-stage crystallization step of crystallizing terephthalic acid after catalytic hydrogenation and has been cooled to temperature between 120 to 200° C., is subjected to a dispersion medium replacement step, i.e., a step of replacing the dispersion medium (first dispersion medium) containing a large amount of impurities with a fresh dispersion medium (second dispersion medium). Subsequently, the resulting slurry containing the terephthalic acid crystal and the second dispersion medium is subjected to solid-liquid separation to obtain the terephthalic acid crystal. When the terephthalic acid slurry resulting from catalytic hydrogenation is subjected to dispersion medium replacement, it is preferable to use water as the second dispersion medium.

The apparatus used to perform the dispersion medium replacement step of the present embodiment, namely the dispersion medium replacement tower, is broadly divided into a tower upper compartment, a tower lower compartment, and a tower middle part. The diameter of the tower middle part can be varied as appropriate depending on the amount of the slurry to be treated and is preferably such that the tower cross-sectional area per throughput of terephthalic acid crystal of 1 t/hr is 0.2 to 2 m². The diameters of the tower upper compartment and tower lower compartment may be similar to that of the tower middle part and can be larger. The tower upper compartment has a portion through which the starting slurry containing the first dispersion medium and terephthalic acid crystal is introduced. This starting slurry introduction portion may open at the inner wall of the tower upper compartment. In order to disperse the crystal well, the starting slurry introduction portion is preferably one extending into and opening at the inside of the tower upper compartment. The opening end may be oriented downwardly. The opening end may be equipped with a mechanism such as a dispersion plate that helps the crystal to disperse. The tower upper compartment further includes a first dispersion medium discharge portion, through which the first dispersion medium containing few terephthalic acid crystals is discharged and introduced into a certain treatment chamber. The tower lower compartment includes a second dispersion medium supply portion, a discharge port through which the terephthalic acid slurry resulting from replacement with the second dispersion medium is discharged, regulators for the flow rate of the second dispersion medium to be supplied and the flow rate of the replaced slurry to be discharged, and a stirring device for the slurry in the tower lower compartment. The discharge port through which the replaced slurry resulting from replacement with the second dispersion medium is discharged is preferably situated, as described above, in the vicinity of the bottom of the tower lower compartment, since the replaced slurry has high specific gravity. The replaced slurry discharged from the lower compartment of the dispersion medium replacement tower is delivered to the crystallization chamber and then to the solid-liquid separation unit, by which crystals of terephthalic acid are separated from the dispersion medium. A solid-liquid separator can be suitably used as the solid-liquid separation unit.

In the method of producing terephthalic acid according to the present embodiment, the conditions and manner of the operation of the dispersion medium replacement tower are important to reduce the impurity content in terephthalic acid and obtain high-purity terephthalic acid. Hereinafter, specific examples of preferred conditions and manner of the operation of the dispersion medium replacement tower will be described.

The terephthalic acid crystal in the starting slurry introduced into the tower upper compartment of the dispersion medium replacement tower gravitationally settle through the tower middle part and come into contact with an upstream flow of the second dispersion medium introduced from a lower part of the tower as a countercurrent. The terephthalic acid crystal having settled to the tower lower compartment is dispersed in the replacing second dispersion medium to form a slurry layer with crystal concentration higher than that in the tower middle part, and the resulting slurry is discharged out of the dispersion medium replacement tower through the slurry discharge portion.

The temperature of the second dispersion medium may be set on similar level of that of the starting slurry introduced into the tower upper compartment. When the temperature of the second dispersion medium is set to temperature 20 to 100° C. below that of the starting slurry, the dispersion medium replacement efficiency can be further improved. In the context of the present application, the dispersion medium replacement efficiency is evaluated using a dispersion medium replacement ratio calculated from the degree of removal of impurities dissolved in the dispersion medium of the starting slurry.

The pressure in the dispersion medium replacement tower needs to be at least sufficient to maintain the temperatures of the starting slurry and second dispersion medium. The upper limit of the pressure is not defined by operational requirements; however, operation at an excessively high pressure requires enhancement of the pressure resistance of the replacement tower, bringing about an increase in equipment cost. The pressure in the dispersion medium replacement tower is preferably 0.1 to 2 MPa (gauge pressure) and more preferably 0.2 to 1.5 MPa.

The linear velocity of the upward flow of the second dispersion medium in the middle part of the dispersion medium replacement tower depends on, for example, the structure of the apparatus and the size of the crystal, and is preferably 0.2 to 1.5 m/hr (superficial velocity) and more preferably 0.5 to 1.0 m/hr. If the linear velocity is excessively low, separation between the first dispersion medium and terephthalic acid crystal will be insufficient, so that the purity of terephthalic acid will be low. An excessively high linear velocity will unfortunately lead to an increase in the amount of the second dispersion medium to be used.

It is important for the layer of the slurry of terephthalic acid crystal in the lower compartment of the dispersion medium replacement tower to maintain its flowability. This is because if the slurry layer formed by settling down of terephthalic acid crystal is fully consolidated, the flowability as slurry is lost, so that the slurry cannot be discharged from the dispersion medium replacement tower by any engineering technique. To prevent this situation, the layer of the slurry of terephthalic acid crystal in the tower lower compartment needs to be always fluidized. Thus, in the dispersion medium replacement tower used in the present embodiment, a stirring blade is provided inside the slurry layer in the tower lower compartment to disperse the contents of the slurry layer well and prevent channeling or uneven flow of the second dispersion medium. The stirring blade provided to impart an appropriate flowability to the slurry layer in the tower lower compartment is not particularly limited and may be any stirring blade having a blade portion extending horizontally from the shaft of the stirring blade. The number and shape of the vanes of the blade portion are not particularly limited and may be such that the blade portion presents a straight-line shape, cross shape, or tomoe shape when viewed from above in the direction of the shaft of the stirring blade. The size of the blade portion of the stirring blade needs to be sufficient to fluidize the whole of the sedimentary layer of terephthalic acid crystal, and is preferably 0.2 to 0.8 times with respect to the diameter of the tower lower compartment of the dispersion medium replacement tower and more preferably 0.3 to 0.7 times with respect to the diameter of the tower lower compartment of the dispersion medium replacement tower.

The rotational speed of the stirring blade is preferably 0.1 to 20 rotations per minute and more preferably 0.5 to 10 rotations per minute. The power of the stirring blade, as expressed by the power per unit volume of the slurry layer in the tower lower compartment, is preferably 0.05 to 1.0 kWh/m$^3$, more preferably 0.1 to 0.8 kWh/m$^3$, and even more preferably 0.2 to 0.7 kWh/m$^3$. When the stirring power is in the range of 0.05 to 1.0 kWh/m$^3$, an appropriate flowability can be imparted to the slurry layer in the tower lower compartment to prevent solidification or adhesion of the slurry and clogging of the discharge port, besides which a high dispersion medium replacement ratio can be achieved.

In order that the second dispersion medium supplied to the lower compartment of the dispersion medium replacement tower may be well distributed in the slurry layer and channeling or uneven flow of the second dispersion medium may be prevented, it is effective to supply the second dispersion medium from the stirring blade provided inside the slurry layer by using the stirring blade in a sprinkler-like fashion or supply the second dispersion medium via a ring-shaped sparger provided inside the sedimentary layer. With these techniques, the flowability of the slurry layer can be maintained to prevent solidification of the slurry and adhesion of the crystal to the tower lower compartment or stirring blade. The uniform distribution of the second dispersion medium in the sedimentary layer of terephthalic acid crystal can prevent channeling of the second dispersion medium and also provide the advantage of making it possible to efficiently clean off various impurities etc. adhering to the crystal surfaces.

The method of producing terephthalic acid according to the present embodiment is capable of adapting, for example, to load fluctuation of terephthalic acid crystal and yielding a high dispersion medium replacement ratio stably over a long period of time, because the dispersion medium replacement step is performed in the manner described below while the operation conditions described hereinbefore are met. To stably keep a high dispersion medium replacement ratio, it is important that the position of the below-described boundary region formed in an upper portion of the slurry layer in the lower compartment of the replacement tower be kept in a certain range and that the concentration of the slurry layer in the tower lower compartment be kept in a certain range.

The boundary region formed in an upper portion of the slurry layer in the tower lower compartment of the dispersion medium replacement tower refers to a boundary region showing a characteristic temperature distribution, namely a sharp change in temperature in the up-down direction, which is caused by increasing the temperature of the upper compartment of the dispersion medium replacement tower relative to the lower compartment of the dispersion medium replacement tower and keeping the slurry concentration in the lower compartment higher than that in the middle part. The position of the boundary region can be detected, for example, by arranging a plurality of thermometers in the vertical direction inside the lower compartment of the dispersion medium replacement tower and thereby measuring the temperature change in the vertical direction inside the dispersion medium replacement tower. That is, in the production method according to the present embodiment, it is preferable that a plurality of thermometers be arranged in the vertical direction inside the lower compartment of the dispersion medium replacement tower to measure the temperature change in the vertical direction inside the dispersion medium replacement tower and thereby detect the position of the interfacial region between the layer of the slurry of terephthalic acid crystal, which is formed in the lower compartment of the dispersion medium replacement tower, and a dilute terephthalic acid slurry in the middle part of the dispersion medium replacement tower.

The plurality of thermometers preferably comprise two or more thermometers and more preferably comprise five or more thermometers.

The position of the boundary region is sensitive to the upward dispersion medium flow inside the tower, and the upward dispersion medium flow inside the tower can be controlled by adjusting the position of the boundary region. The position of the boundary region is elevated as the upward dispersion medium flow becomes stronger, and is lowered as the upward dispersion medium flow becomes weaker. Thus, detection of lowering of the position of the boundary region indicates a decrease in the rate of the upward dispersion medium flow. When the rate of the upward dispersion medium flow is decreased, a process for increasing the rate of the upward dispersion medium flow is performed. Examples of the process for increasing the rate of the upward dispersion medium flow include: increasing the amount of the second dispersion medium to be supplied; and performing a procedure for decreasing the flow rate of the replaced slurry to be discharged. Increasing the amount of the second dispersion medium to be supplied is preferred. When the position of the interfacial region is adjusted by the procedure for decreasing the flow rate of the replaced slurry to be discharged, the dispersion medium replacement ratio may decrease and thus the quality of terephthalic acid may deteriorate. This is why it is preferable to adjust the interfacial position by the amount of the second dispersion medium to be supplied.

The position of the boundary region is preferably above the upper end of the stirrer disposed in the lower compartment of the dispersion medium replacement tower in the range of 0.3 to 1.5 times with respect to the inner diameter of the replacement tower from the upper end. The position of the boundary region is preferably adjusted to lie within the variation range of ±800 mm from the target level and more preferably adjusted to lie within the variation range of ±500 mm from the target level.

To adjust the temperature distribution in the vertical direction inside the dispersion medium replacement tower so that its upper part has higher temperature, the temperature of the second dispersion medium may be set lower than the temperature of the supplied slurry. By adjusting the temperature distribution in the vertical direction inside the dispersion medium replacement tower so that its upper part has higher temperature, not only can the replacement efficiency of the dispersion medium replacement apparatus be kept high, but also the specific gravity of the dispersion medium of the slurry in the lower compartment can be made higher than the specific gravity of the dispersion medium of the supplied slurry, so that a more stable system can be formed.

A possible technique for keeping the concentration of the slurry layer in the tower lower compartment within a certain range is, for example, to directly measure the concentration of the slurry layer in the tower lower compartment and, on the basis of the measured concentration, regulate the flow rate of the slurry to be discharged or the flow rate of the second dispersion medium to be supplied. However, with this technique in which the concentration of the slurry layer in the tower lower compartment is directly measured, the measured value of the concentration of the slurry layer in the tower lower compartment varies so significantly that the concentration-based regulation of the flow rate of the slurry to be discharged or the flow rate of the second dispersion medium to be supplied is difficult. In addition, direct measurement of the concentration of the slurry layer in the tower lower compartment tends to suffer from clogging of the piping for concentration measurement.

In the present embodiment, the measurement of the slurry concentration is preferably performed on the slurry in the crystallization chamber into which the slurry containing terephthalic acid crystal and the second dispersion medium is discharged from the replacement tower. Specifically, a densitometer is disposed in a slurry discharge pipe for discharge from the crystallization chamber, and the slurry concentration is calculated from the measured slurry density. More preferably, a densitometer is disposed in a pipe branching from the slurry discharge pipe for discharge from the crystallization chamber and designed to circulate the slurry into the crystallization chamber. When the concentration of the slurry in the crystallization chamber is measured, the slurry concentration measurement can be conducted with reduced variation, and thus the variation of slurry concentration inside the replacement tower can be reduced, so that stable control can be accomplished.

In the present embodiment, the slurry concentration measured by a densitometer in the crystallization chamber is in the range of 25 to 40 mass %, as expressed by the mass percentage of terephthalic acid crystal in the slurry. If the slurry concentration is lower than 25 mass %, the amount of wastewater to be treated in the subsequent solid-liquid separation step increases, which causes a load increase. If the slurry concentration is higher than 40 mass %, the viscosity of the slurry increases, which raises the likelihood of defects such as an increase in differential pressure inside the piping and clogging of the piping. In order to limit the load increase in the solid-liquid separation step and prevent the differential pressure increase or clogging of the slurry piping, the slurry concentration is preferably in the range of 30 to 40 mass %.

In the present embodiment, the volume $V_1$ of the terephthalic acid slurry in the crystallization chamber is regulated and kept in the range of 0.050 to 0.80 times with respect to the volume $V_0$ of the terephthalic acid slurry in the dispersion medium replacement tower in order to stably control the slurry concentration in the dispersion medium replacement tower. If the slurry volume $V_1$ in the crystallization chamber is excessively small, the variation of slurry concentration becomes so large that control of the slurry concentration in the dispersion medium replacement tower is difficult. If the slurry volume $V_1$ in the crystallization chamber is excessively large, the variation of the detected slurry concentration becomes so small that control of the slurry concentration in the dispersion medium replacement tower is difficult. Thus, from the viewpoint of the ease of control of the slurry concentration in the dispersion medium replacement tower, $V_1$ is in the range of 0.050 to 0.80 times with respect to $V_0$ and preferably in the range of 0.10 to 0.50 times with respect to $V_0$.

Hereinafter, a preferred example shown in FIG. 1 of the present embodiment will be described. In FIG. 1, the volume $V_0$ of the terephthalic acid slurry in the dispersion medium replacement tower 1 corresponds to the volume of the portion of the replacement tower that is situated below the starting slurry introduction nozzle 3. The slurry volume $V_1$ in the crystallization chamber 11 is adjusted in the range of 0.050 to 0.80 times with respect to $V_0$, and thus control of the slurry concentration of the slurry layer b in the lower compartment of the replacement tower is facilitated.

The densitometer 12 is disposed in a pipe branching from a pipe for discharge and transfer of the terephthalic acid slurry from the bottom of the crystallization chamber 11 to the subsequent step and designed to circulate the slurry into the crystallization chamber 11. The operation is performed in such a manner that the slurry density as measured by the densitometer 12 is kept within a certain range and that the position a of the boundary region which is determined with the aid of thermometers provided in the dispersion medium replacement tower is in the variation range of ±800 mm from a target level located above the upper end of the stirrer 8 with 0.3 to 1.5 times as long as the inner diameter of the replacement tower. The operation in this manner enables to continuously maintain an extremely high replacement efficiency. Upon increase in slurry density, the flow rate through the purified terephthalic acid slurry discharge port 5 may be increased and then kept constant. The opposite procedure may be performed upon decrease in slurry density. It is preferable to increase the amount of the second dispersion medium to be supplied upon lowering of the position a of the boundary region of the slurry layer in the lower compartment of the replacement tower and decrease the amount of the second dispersion medium to be supplied upon elevation of the position a of the boundary region.

In the method of producing terephthalic acid according to the present embodiment, 1) the position of the boundary region formed in the upper portion of the slurry layer in the lower compartment of the replacement tower is kept within a certain range, and 2) the slurry volume of the terephthalic acid slurry discharged from the lower compartment of the replacement tower and held in the crystallization chamber is kept within the range of 0.050 to 0.80 times with respect to the volume of the terephthalic acid slurry in the dispersion medium replacement tower while the slurry concentration in the crystallization chamber is kept in the range of 25 to 40 mass %, so that the concentration of the slurry layer in the tower lower compartment is controlled within a certain range.

Consequently, a high dispersion medium replacement ratio can be stably maintained over a long period of time, and high-quality terephthalic acid can be obtained.

EXAMPLES

Next, the present invention will be described more specifically using examples. It should be noted that the present invention is not limited by these examples.

The dispersion medium replacement ratio determined in the examples described below is the ratio of the amount of benzoic acid contained in the replaced dispersion medium overflowing through the first dispersion medium outlet port 4 to the amount of benzoic acid contained as a by-product in the dispersion medium of the starting slurry.

The aqueous terephthalic acid slurry used in the examples was produced in the following manner. First, an oxidation step was performed in which a liquid-phase oxidation reaction of p-xylene or the like was allowed to take place using an acetic acid solvent and which was followed by a crystallization step in which crude terephthalic acid was crystallized by cooling. The crystal of the resulting crude terephthalic acid were separated in a separation step and dried in a drying step followed by a hydrogenation step in which the crude terephthalic acid was purified by a catalytic hydrogenation reaction in the presence of an aqueous solvent to give aqueous solution of purified terephthalic acid. This aqueous solution was subsequently subjected to a crystallization step, and thus the aqueous terephthalic acid slurry was obtained.

Example 1

The apparatus shown in FIG. 1 was used to conduct an experiment in which the dispersion medium of the aqueous terephthalic acid slurry obtained through the hydrogenation and crystallization steps was replaced with clean water. In FIG. 1, the dispersion medium replacement tower 1 was a stainless steel vessel, the tower diameter was 4 m, and the terephthalic acid slurry volume $V_0$ inside the replacement tower was 86 m$^3$. The nozzle 3 for introducing the aqueous terephthalic acid slurry as a starting material (this slurry may hereinafter be referred to as "starting slurry") was disposed inside the upper part of the dispersion medium replacement tower, and this starting slurry introduction nozzle 3 was connected to the starting slurry supply pump 2. The dispersion medium outlet port 4 was provided at the top of the tower. The lower compartment of the dispersion medium replacement tower was in the form of a semi-elliptical bowl, and the purified terephthalic acid slurry resulting from dispersion medium replacement was discharged through the purified terephthalic acid slurry discharge port 5. The flow rate through the discharge port 5 was able to be controlled by a valve provided downstream. The stirring blade 8 used was a stirring blade having a 2-m-diameter blade portion consisting of four 45-degree-inclined vanes arranged to present a cross shape. The lower side of each vane had second dispersion medium introduction ports 9 which were evenly distributed and the number of which was 12. A thermometer 10 was disposed on the inner wall at a position 0.3 m above the upper end of the stirring blade 8 and, starting from this thermometer, a total of seven thermometers 10 were arranged at regular intervals of 1 m in the upward direction to measure the temperature distribution. The slurry discharged through the purified terephthalic acid slurry discharge port 5 was led to the crystallization chamber 11 and subjected to further crystallization. The pipe for discharge and transfer of the purified terephthalic acid slurry from the bottom of the crystallization chamber 11 to the subsequent step was branched to circulate a part of the purified terephthalic acid slurry into the crystallization chamber 11. The slurry densitometer 12 was disposed in the circulation pipe to enable slurry density measurement.

First, the water supply pump 6 in FIG. 1 was driven to feed water at 100° C. into the system through the second dispersion medium introduction ports 9 at a rate of 80 m$^3$/h. Once the water began to overflow through the dispersion medium outlet port 4, the motor 7 was actuated to rotate the stirring blade 8 at a speed of eight rotations per minute. Subsequently, the starting slurry supply pump 2 was actuated to supply the starting slurry at 165° C. through the starting slurry introduction nozzle 3 at 109 m$^3$/h, and the slurry discharge through the slurry discharge port 5 was started with the discharge flow rate set at 100 m$^3$/h. Once the slurry volume $V_1$ in the crystallization chamber 11 reached 30 m$^3$, the slurry discharge from the crystallization chamber 11 was started to supply the slurry to a solid-liquid separator. Afterwards, the amount of the slurry discharged to the solid-liquid separator was regulated to maintain the slurry volume $V_1$ in the crystallization chamber 11. Additionally, the flow rate through the slurry discharge port 5 of the dispersion medium replacement tower was regulated to adjust the value measured by the densitometer 12 disposed in the crystallization chamber 11 to 30 mass % or more, and the value was stabilized in the range of 31 to 32 mass %. Based on the indication by the thermometers 10, the flow rate of the second dispersion medium introduction pump 6 was regulated so that the interfacial region was located between the second-lowermost and third-lowermost thermometers.

After the system reached a steady state, the instantaneous values of the various flow rates were read as follows: 109 m$^3$/h for the starting slurry supply pump 2, 97 m$^3$/h for the purified terephthalic acid slurry discharge port 5, 75 m$^3$/h for the water supply pump 6, and 88 m$^3$/h for the overflow through the dispersion medium outlet port 4. The value of the densitometer 12 disposed in the crystallization chamber 11 was 31.6 mass %, and the values of the thermometers 10 of the dispersion medium replacement apparatus were 133° C., 150° C., 161° C., 162° C., 161° C., 162° C., and 163° C. in order from the lowermost thermometer. The interfacial region was thus determined to be located at a height between the second-lowermost and third-lowermost thermometers. After the steady state was reached, the dispersion medium replacement ratio was able to be kept stably in the range of 93% to 96%.

Comparative Example 1

The dispersion medium replacement tower was operated in the same manner as in Example 1, except that control of the interfacial position was attempted by fixing the starting slurry supply rate at 109 m$^3$/h, fixing the flow rate of the second dispersion medium supply pump 6 at 75 m$^3$/h, and regulating the flow rate through the purified terephthalic acid slurry discharge port 5 in the range of 95 to 100 m$^3$/h. The value of the densitometer 12 was in the range of 31 to 32 mass %; however, the interfacial position varied between the lowermost thermometer and the third-lowermost thermometer, namely in the range of about ±1000 mm from the control target level, and the replacement ratio varied in the range of 86 to 95%.

Comparative Example 2

The dispersion medium replacement tower was operated in the same manner as in Example 1, except that the amount of the slurry discharged from the crystallization chamber was regulated so that the slurry volume $V_1$ in the crystallization chamber was 4 m³. Regulation of the flow rate through the slurry discharge port 5 of the dispersion medium replacement tower was attempted to keep the value of the densitometer 12 in the range of 31 to 32 mass %; however, the value of the densitometer 12 varied in the range of 29 to 35%, and the dispersion medium replacement ratio varied in the range of 82 to 90%.

Comparative Example 3

The dispersion medium replacement tower was operated in the same manner as in Example 1, except that the amount of the slurry discharged from the crystallization chamber was regulated so that the slurry volume $V_1$ in the crystallization chamber was 80 m³. During the operation, the flow rate through the slurry discharge port 5 of the dispersion medium replacement tower was regulated to keep the value of the densitometer 12 in the range of 31 to 32 mass %. However, the dispersion medium replacement ratio varied in the range of 85 to 95%. When the amount of the slurry held in the crystallization chamber was excessively large, the variation of dispersion medium replacement ratio was large despite the slurry concentration being stable.

The present application is based on Japanese Patent Application filed with the Japan Patent Office on Mar. 31, 2016 (Japanese Patent Application No. 2016-071319), the contents of which are incorporated herein by reference.

REFERENCE SIGNS LIST

1 Dispersion medium replacement tower
2 Starting slurry supply pump
3 Starting slurry introduction nozzle
4 Dispersion medium outlet port
5 Purified terephthalic acid slurry discharge port
6 Second dispersion medium supply pump
7 Motor
8 Stirring blade
9 Second dispersion medium introduction port
10 Thermometer
11 Crystallization chamber
12 Slurry densitometer
a Boundary region of slurry layer
b Terephthalic acid crystal slurry layer

The invention claimed is:

1. A method of producing terephthalic acid, comprising:
introducing starting terephthalic acid slurry into an upper part of a dispersion medium replacement tower, the starting terephthalic acid slurry comprising a dispersion medium and crude terephthalic acid obtained through liquid-phase oxidation of a p-phenylene compound;
bringing the starting terephthalic acid slurry into contact with an upward flow of a second dispersion medium introduced from a lower part of the dispersion medium replacement tower to form, in a lower compartment of the dispersion medium replacement tower, a layer of slurry of a purified terephthalic acid crystal dispersed in the second dispersion medium;
discharging the slurry of the purified terephthalic acid crystal from the lower compartment of the dispersion medium replacement tower and delivering the slurry to a crystallization chamber provided with a unit for measuring slurry concentration; and
delivering the slurry in the crystallization chamber to a solid-liquid separation unit to separate a terephthalic acid crystal,
wherein
the following conditions (1) to (3) are maintained by regulating a flow rate of the second dispersion medium supplied to the lower compartment of the dispersion medium replacement tower, the flow rate of the slurry of the purified terephthalic acid crystal which is discharged from the lower compartment of the dispersion medium replacement tower, and the flow rate of the slurry delivered from the crystallization chamber to the solid-liquid separation unit:
(1) volume $V_1$ of the slurry in the crystallization chamber is in a range of 0.050 to 0.80 times with respect to volume $V_0$ of the whole terephthalic acid slurry in the dispersion medium replacement tower;
(2) a position of an interfacial region between the layer of the slurry of terephthalic acid crystal which is formed in the lower compartment of the dispersion medium replacement tower and a dilute terephthalic acid slurry in a middle part of the dispersion medium replacement tower is in a variation range of ±800 mm from a control target level; and
(3) the slurry concentration in the crystallization chamber is in a range of 25 to 40 mass %.

2. The method of producing terephthalic acid according to claim 1, wherein
a stirrer is disposed in the lower compartment of the dispersion medium replacement tower, and
the position of the interfacial region between the layer of the slurry of terephthalic acid crystal which is formed in the lower compartment of the dispersion medium replacement tower and the dilute terephthalic acid slurry in the middle part of the dispersion medium replacement tower is above an upper end of the stirrer in a range of 0.3 to 1.5 times with respect to an inner diameter of the replacement tower.

3. The method of producing terephthalic acid according to claim 1, wherein the slurry concentration in the crystallization chamber is kept in the range of 25 to 40 mass % by:
increasing a slurry flow rate of the slurry of the purified terephthalic acid crystal to be discharged from the lower compartment of the dispersion medium replacement tower upon increase in the concentration of the slurry in the crystallization chamber; and
decreasing the slurry flow rate upon decrease in the slurry density.

4. The method of producing terephthalic acid according to claim 1, wherein the position of the interfacial region between the layer of the slurry of terephthalic acid crystal which is formed in the lower compartment of the dispersion medium replacement tower and the dilute terephthalic acid slurry in the middle part of the dispersion medium replacement tower is kept in the variation range of ±800 mm from the control target level by:
decreasing the flow rate of the second dispersion medium supplied to the lower compartment of the dispersion medium replacement tower upon elevation of the position of the interfacial region; and
increasing the flow rate upon lowering of the position of the interfacial region.

5. The method of producing terephthalic acid according to claim 1, wherein
the unit for measuring the slurry concentration in the crystallization chamber is a densitometer, and the densitometer is disposed in a pipe provided to discharge the slurry of the purified terephthalic acid crystal from the crystallization chamber and designed to circulate a part of the slurry into the crystallization chamber.

6. The method of producing terephthalic acid according to claim 1, wherein
a plurality of thermometers are arranged in a vertical direction inside the dispersion medium replacement tower, and
the position of the interfacial region between the layer of the slurry of terephthalic acid crystal which is formed in the lower compartment of the dispersion medium replacement tower and the dilute terephthalic acid slurry in the middle part of the dispersion medium replacement tower is detected by measuring a temperature change in the vertical direction inside the dispersion medium replacement tower.

7. The method of producing terephthalic acid according to claim 1, wherein the starting terephthalic acid slurry is slurry obtained by a process comprising:
forming crude terephthalic acid slurry through liquid-phase oxidation of a p-phenylene compound followed by depressurization and heating to high temperature;
separating a reaction dispersion medium from the crude terephthalic acid slurry to obtain a crude terephthalic acid crystal;
dissolving the crude terephthalic acid crystal in water at high temperature and high pressure;
subjecting the resulting solution to catalytic hydrogenation; and
subjecting the resulting reaction fluid to gradual depressurization and cooling using a multi-stage crystallization chamber to crystallize terephthalic acid.

* * * * *